(12) United States Patent
Ju et al.

(10) Patent No.: US 10,584,361 B2
(45) Date of Patent: Mar. 10, 2020

(54) ALGAE HAVING INTRACELLULAR LIPID PARTICLES AND HIGH LIPID CONTENT

(71) Applicants: Lu-Kwang Ju, Akron, OH (US); Cong Li, Akron, OH (US)

(72) Inventors: Lu-Kwang Ju, Akron, OH (US); Cong Li, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 336 days.

(21) Appl. No.: 13/959,098

(22) Filed: Aug. 5, 2013

(65) Prior Publication Data

US 2014/0038247 A1 Feb. 6, 2014

Related U.S. Application Data

(60) Provisional application No. 61/679,692, filed on Aug. 4, 2012.

(51) Int. Cl.
*C12P 7/64* (2006.01)

(52) U.S. Cl.
CPC .............. *C12P 7/649* (2013.01); *C12P 7/6463* (2013.01); *Y02E 50/13* (2013.01)

(58) Field of Classification Search
USPC ......................................................... 435/134
See application file for complete search history.

(56) References Cited

U.S. PATENT DOCUMENTS

| | | | | |
|---|---|---|---|---|
| 7,816,570 | B2 * | 10/2010 | Roberts, IV | C10G 45/58 |
| | | | | 585/14 |
| 8,313,647 | B2 * | 11/2012 | Kale | C11B 1/10 |
| | | | | 210/634 |
| 2012/0088279 | A1 * | 4/2012 | Swanson | C12P 7/6463 |
| | | | | 435/134 |
| 2012/0130099 | A1 * | 5/2012 | Wittenberg | C11B 1/06 |
| | | | | 554/8 |
| 2012/0178123 | A1 * | 7/2012 | Rosen | C12M 21/02 |
| | | | | 435/42 |

FOREIGN PATENT DOCUMENTS

WO WO 2010132413 A1 * 11/2010 ............ C12P 7/6463

OTHER PUBLICATIONS

Floder, Sabine et al. Energy Dependent Bacterivory in Ochromonas minima: A Strategy Promoting the Use of Substitutable Resources and Survival at Insufficient Light Supply. Protist. Elsevier. 2006.*
Floder (Energy Dependent Bacterivory in Ochromonas minima: A Strategy Promoting the Use of Substitutable Resources and Survival at Insufficient Light Supply, 2006).*

* cited by examiner

*Primary Examiner* — Nghi V Nguyen
(74) *Attorney, Agent, or Firm* — Renner Kenner Greive Bobak Taylor & Weber

(57) ABSTRACT

A method for increasing the lipid content of algae includes combining algae and a lipid-precipitating addition in a growth-inhibitive medium, the growth-inhibitive medium being deficient in at least one nutrient that is necessary for reproductive growth of algae, thus frustrating algae reproduction, the lipid-precipitating addition selected from hydroxyl-containing compounds and amine-containing compounds. An organic acid addition may also be combined with the lipid-precipitating addition and algae in the growth-inhibitive medium, the organic acid addition including compounds containing carboxylic acid functionality. Direct production of biodiesel is also achieved by the use of particular lipid-precipitating additions and organic acid additions.

18 Claims, 6 Drawing Sheets

ALGAE HAVING INTRACELLULAR LIPID PARTICLES AND HIGH LIPID CONTENT

CROSS-REFERENCE TO RELATED APPLICATION

This application claims priority to U.S. Provisional Patent Application No. 61/679,692 filed on Aug. 4, 2012, the contents of which are incorporated herein by reference.

FIELD OF THE INVENTION

The present invention generally relates to the production of algae having high lipid content. The present invention further relates to the direct formation of biodiesel by algae.

BACKGROUND OF THE INVENTION

Lipids, with various physiological functions, are a major group of materials present in biological systems, besides proteins, saccharides, and nucleic acids. Lipids also represent an important group of industrial products manufactured for nutritional, medical, cosmetic, hygienic, environmental, and numerous other applications. Some important examples of lipids for nutritional and medical uses include the mono-saturated lipids for healthy diets, which offer the following potential benefits: decreased risk of breast cancer, heart disease and stroke; reduced cholesterol levels and belly fat; less pain and stiffness for those with rheumatoid arthritis; and weight loss; and the omega-3 fatty acids, e.g., docosahexaenoic acid (DHA), with reported health benefits to brain, eye and heart, and included in infant formula.

More recently, with the heightened awareness of global warming and depleting petroleum sources, there has been very strong demand for production of renewable fuel and chemicals. Large-scale industrial production of lipids using microorganisms plays an important role in meeting this demand. For renewable fuel the microbial lipids can be converted to biodiesel (methyl or ethyl esters of fatty acids), hydrocarbons, and jet fuel. The lipids can also serve as feedstock for the production of various chemicals. For industrial production processes, the productivity, product concentration and yield (i.e., percent conversion of substrate to product) are very important factors to be maximized for overall economics. One common limitation in microbial processes for production of intracellular lipids is the low intracellular lipid contents achievable.

Thus lipid content should be maximized for economic purposes, i.e., high productivity, high product concentrations, and high yield (i.e., % conversion of substrate to product). However, beyond certain concentrations, organic acids are inhibitory/toxic to cells themselves. This can limit lipid contents inside the cells. The present invention induces formation of insoluble lipid droplets/particles in algae so the lipid contents can be very high.

SUMMARY OF THE INVENTION

The present invention provides methodologies for the formation of "insoluble" lipid particles or droplets inside the cells of algae. Dissolved lipids at concentrations beyond certain levels are inhibitory or even toxic to organisms, at least by lowering intracellular pH and denaturing/inhibiting activities of enzymes and other biological molecules. Formation of insoluble lipid particles or droplets avoids such negative effects. Therefore, this technology leads to very high intracellular lipid contents (>50-80% of cell dry weight) and improves the productivity and product yield of the processes. The high intracellular lipid contents also significantly reduce the unit cost of downstream lipid collection and separation. The present invention provides faster formation of lipid particles/droplets from organic materials by heterotrophic and phagotrophic microalga, instead of the known slow lipid accumulation by certain photosynthetic microalga under the limitation of certain nutrient (more commonly N-source or Si-source)

In a first embodiment, the present invention provides a method for increasing the lipid content of algae comprising the steps of combining algae and a lipid-precipitating addition in a growth-inhibitive medium, said growth-inhibitive medium being deficient in at least one nutrient that is necessary for reproductive growth of algae, thus frustrating algae reproduction, said lipid-precipitating addition selected from hydroxyl-containing compounds and amine-containing compounds.

In a second embodiment, the present invention provides a method as in the first embodiment, wherein the algae is selected from the group consisting of phagotrophic algae and osmotrophic algae.

In a third embodiment, the present invention provides a method as in either the first or second embodiment, wherein the algae is selected from *Ochromonas* species.

In a fourth embodiment, the present invention provides a method as in any of the first through third embodiments, wherein the lipid-precipitating addition includes a hydroxyl-containing compound selected from the group consisting of glycerol, methanol, ethanol, dihydroxyethane, propanol, isopropanol, cyclopropanol, propylene glycol, butanol, isobutanol, cyclobutanol, dihydroxybutanes, trihydroxybutanal, cyclohexanol, dihydroxycyclohexanes, phenol, dihydroxybenzenes, and trihydroxybenzenes.

In a fifth embodiment, the present invention provides a method as in any of the first through fourth embodiments, wherein the lipid-precipitating addition includes amine-containing compounds selected from the group consisting of ammonia, methylamine, dimethylamine, ethanolamine, methylethanolamine, aniline, diphenylamine, amino acids, peptides, biogenic amines (such as histamine), urea, acetamide, cyclic secondary amines, cyclic secondary amides.

In a sixth embodiment, the present invention provides a method as in any of the first through fifth embodiments, wherein the growth-inhibitive medium is water based.

In a seventh embodiment, the present invention provides a method as in any of the first through sixth embodiments, wherein the growth-inhibitive medium is selected from distilled water, deionized water, tap water, river water, lake water, and sea water.

In an eighth embodiment, the present invention provides a method as in any of the first through seventh embodiments, wherein the growth-inhibitive medium is a salt solution.

In a ninth embodiment, the present invention provides a method as in any of the first through eighth embodiments, wherein the growth-inhibitive medium includes one or more mineral salts.

In a tenth embodiment, the present invention provides a method as in any of the first through ninth embodiments, wherein the one or more mineral salt is selected from the group consisting of ammonium chloride, potassium phosphate, magnesium sulfate, magnesium carbonate, calcium carbonate, sodium chloride, potassium chloride, ferric chloride, manganese chloride, manganese sulfate, copper sulfate, zinc sulfate, cobalt sulfate, boric acid, ammonium heptamolybdate, and sodium vanadate.

In an eleventh embodiment, the present invention provides a method as in any of the first through tenth embodiments, wherein the at least one nutrient deficient in the growth-inhibitive medium is selected from the group consisting of nitrogen, phosphorus, magnesium, sulfur, and calcium.

In a twelfth embodiment, the present invention provides a method as in any of the first through eleventh embodiments, further comprising combining an organic acid addition with the algae and the lipid-precipitating addition in the growth-inhibitive medium, the organic acid addition including compounds containing carboxylic acid functionality.

In a thirteenth embodiment, the present invention provides a method as in any of the first through twelfth embodiments, wherein the compounds containing carboxylic acid functionality are selected from organic acids, salts of organic acids and mixtures thereof.

In a fourteenth embodiment, the present invention provides a method as in any of the first through thirteenth embodiments, wherein the organic acid addition is chosen from carboxylic acids, amino acids, sugar acids, peptides, proteins, waste oils, nucleic acids, carboxyl-containing polysaccharides, and other carboxyl-containing materials.

In a fifteenth embodiment, the present invention provides a method as in any of the first through fourteenth embodiments, wherein the organic acid addition is a waste oil selected from grease, waste cooking oil, waste processing oil, waste machinery oil, crude oil sludge, petroleum refinery oil sludge, biodiesel waste oil stream, and oil and grease collected from municipal and industrial wastewater.

In a sixteenth embodiment, the present invention provides a method as in any of the first through fifteenth embodiments, wherein the algae includes osmotrophic algae and the compounds containing carboxylic acid functionality have lengths of from C2 to C7.

In a seventeenth embodiment, the present invention provides a method as in any of the first through sixteenth embodiments, wherein the compounds containing carboxylic acid functionality are selected from acetic acid, propanoic acid, isopropanoic acid, butanoic acid, isobutanoic acid, pyruvic acid, citric acid, isocitric acid, fumaric acid, malic acid, oxaloacetic acid, succinic acid, malonic acid, ketoglutaric acid, cyclopentanoic acid, cyclohexanoic acid, benzoic acid, and phenolcarboxylic acids.

In an eighteenth embodiment, the present invention provides a method as in any of the first through seventeenth embodiments, wherein the algae is phagotrophic, the compounds containing carboxylic acid functionality have lengths of from C8 or larger and are soluble, colloidal, or insoluble compounds consumable by the phagotrophic alga.

In a nineteenth embodiment, the present invention provides a method as in any of the first through eighteenth embodiments, wherein the lipid-precipitating addition is selected from the group consisting of methanol and ethanol, the method further comprising the steps of: accumulating free fatty acid inside the algae, neutralizing the accumulated free fatty acid with the hydroxyl group of the methanol or ethanol, and producing methyl ester.

In a twentieth embodiment, the present invention provides a method as in any of the first through nineteenth embodiments, wherein the produced methyl ester can be extracted and directly used as biodiesel without any transesterification or esterification.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
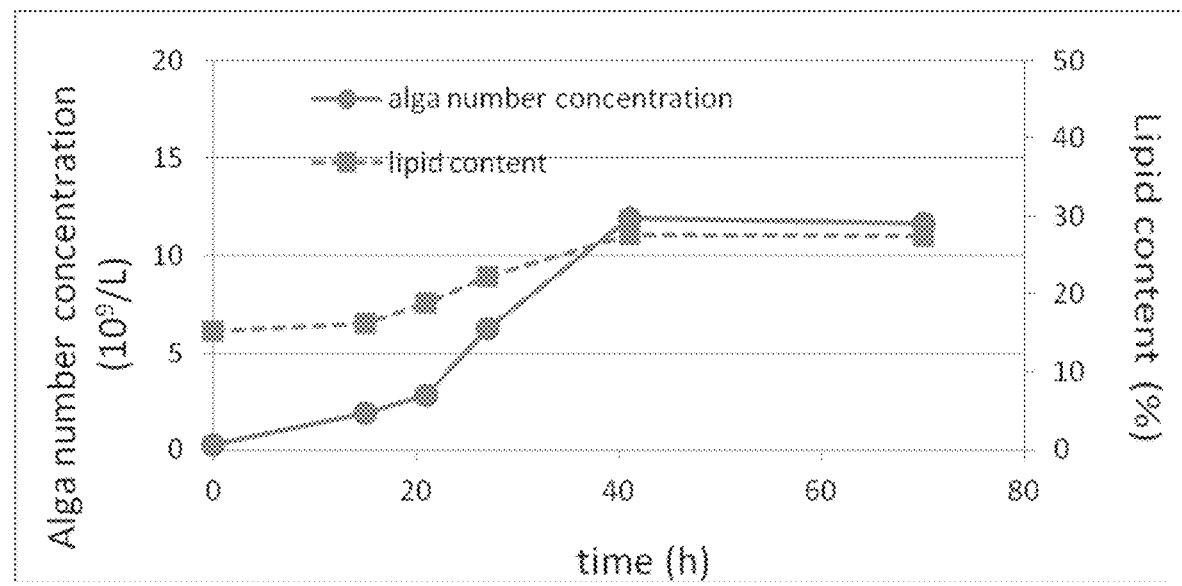
FIG. 1 is a graph showing alga growth profiles with *E. coli* as the nutrient source.

The present invention relates to methods for increasing the lipid content of algae. The method involves combining algae and a lipid-precipitating addition in a growth-inhibitive medium. As used herein, the term growth-inhibitive means inhibiting reproductive growth of algae, i.e., the population of algae, not the size or mass of individual algae. The lipid-precipitating addition is taken in by the algae, resulting in the existence of insoluble lipids within the cells of the algae. In some embodiments, an organic acid addition is combined with the algae and lipid-precipitation addition, with improved insoluble lipid content resulting.

The objective of the present invention is to provide a high percentage of lipids in algae. The lipids can then be beneficially harvested through known techniques, such as, for example, extraction and/or mechanical pressing. The lipids may be useful, for example, for processing into biofuel. Although algae tend to self regulate to a lipid percentage of around 20-30% by dry weight, the present invention provides the ability to produce algae having a higher lipid percentage. Unexpectedly, this invention is able to produce algae having a lipid percentage of 50% or more. In one or more embodiments, algae have a lipid percentage of 60% or more, in other embodiments, 70% or more, and, in other embodiments, 80% or more.

It was found that utilizing a growth-inhibitive medium frustrates algae reproduction and promotes the production of insoluble lipids inside cells of the algae. It was also found that combining an organic acid addition with the algae and the lipid-precipitating addition further promotes the production of insoluble lipids inside cells of the algae. The higher lipid percentages are reached when the organic acid addition is also employed.

Without being bound to any theory, it is hypothesized that the algae take in the organic substrates present in the surrounding environment, and, being frustrated from reproductive growth, simply grow in mass through lipid production. The short- and long-chain organic acids synthesized in the lipid production process can undesirably lower the intracellular pH and, thus, inhibit rate and extent of the synthesis of these organic acids. It is hypothesized that the lipid-precipitation addition taken in by the algae neutralizes and/or reacts with the organic acids synthesized and, accordingly, removes or reduces the self-regulation of lipid production. It is further theorized that the effect of the lipid-precipitating addition is catalyzed or otherwise affected by the algae's enzymes, resulting in the algae storing insoluble lipids inside the cells of the algae. It is likewise theorized that the further organic acid addition is taken in by the algae, resulting in the promotion of lipid production and storage. It is observed that the intracellular lipid particles/droplets are present as numerous small particles/droplets inside the algae cells, instead of one large combined/coalesced particle/droplet per cell. This is very beneficial. If present as one large particle/droplet, particularly when the lipid content is higher than 50%, the large particle/droplet can exert high, unevenly distributed stress to the cell membrane/envelope and other organelles inside the cells. It is hypothesized that the algae have special mechanisms to prevent the lipids from combining/coalescing into large sizes and create the finely distributed, almost uniform, particles/droplets The growth-inhibitive medium is any medium capable of physiologically supporting algae. In some embodiments, the growth-inhibitive medium is water based. In other embodiments the growth inhibitive medium is a salt solution.

In some embodiments, the growth-inhibitive medium includes water selected from distilled water, deionized water, tap water, river water, lake water, sea water and any water from natural water bodies without significant amounts of chemical contents to support heterotrophic growth of algae (thus being growth-inhibitive).

In some embodiments, the growth-inhibitive medium includes water containing one or more mineral salts. In embodiments where the growth-inhibitive medium is deficient in nitrogen, the growth-inhibitive medium excludes salts that can be used as major nitrogen source by algae (or other microorganisms, if the medium was not sterilized or disinfected) for growth. That is, the salts should not contribute nitrogen above the threshold amount necessary for promotion of reproductive growth These non-nitrogen-source mineral salts can include, but are not limited to, one or more of the following: potassium phosphate, magnesium sulfate, magnesium carbonate, calcium carbonate, sodium chloride, potassium chloride, ferric chloride, manganese chloride, manganese sulfate, copper sulfate, zinc sulfate, cobalt sulfate, boric acid, and sodium vanadate.

In embodiments where the growth-inhibitive medium is deficient in phosphorus, the growth-inhibitive medium excludes salts that can be used as major phosphorus source by algae (or other microorganisms, if the medium was not sterilized or disinfected) for growth. That is, the salts should not contribute phosphorus above the threshold amount necessary for promotion of reproductive growth.

These non-phosphorus-source mineral salts can include, but are not limited to, one or more of the following: ammonium chloride, magnesium sulfate, magnesium carbonate, calcium carbonate, sodium chloride, potassium chloride, ferric chloride, manganese chloride, manganese sulfate, copper sulfate, zinc sulfate, cobalt sulfate, boric acid, ammonium heptamolybdate, and sodium vanadate.

In general, where the growth-inhibitive medium is to be deficient in a given nutrient, the growth-inhibitive medium can include appropriate mineral salts though devoid of salts that provide an above-threshold amount of that nutrient.

In some embodiments, the growth-inhibitive medium further includes organic compounds, such as growth factors, vitamins, amino acids, and others, that facilitate cell activities, including longer-term survival without growth and lipid synthesis, but are not as major carbon or energy source. These organic compounds can include, but are not limited to, one or more of the following: nitrilotriacetic acid, biotin, thiamine, glycine, citrate, L-arginine, L-glutamic acid, L-histidine, and DL-methionine.

In some embodiments, the growth-inhibitive is sterilized or disinfected, by autoclaving, pasteurizing, filtering, boiling, treating with acids or bases for necessary periods of time (with or without heating) and then neutralizing prior to use, ozonizing, treating with other disinfecting chemicals for necessary periods of time and then removing the chemicals prior to use, and other sterilization and disinfection methods known to people in the related fields.

The growth-inhibitive medium is deficient in at least one nutrient that is necessary for reproductive growth of the algae. This deficiency promotes the production of lipids inside the algae. The at least one nutrient can be any nutrient that is physiologically required by algae. The growth-inhibitive medium can have any nutrients that are physiologically required by algae, so long as the medium is deficient in at least one nutrient that is necessary for reproductive growth of the algae.

It is easier to control or limit reproductive growth by controlling a deficiency in certain nutrients as compared to others. Particularly, it is easier to control or limit reproductive growth by providing a deficiency in those nutrients that are required in higher concentrations to promote reproductive growth as opposed to those nutrients that are required in relatively lower concentrations to promote reproductive growth. Those nutrients for which a higher concentration is required are more easily reduced below a threshold that results in frustrating algae reproduction. In the same way, the trace nutrients that the algae need for reproductive growth are more difficult to reduce below a necessary threshold that frustrates algae reproduction.

Nutrients that are easier to control include nitrogen and phosphorus. Again, these are easier to control to a threshold deficiency because algae generally require more of these nutrients.

Nutrients that are harder to control include calcium, magnesium, sulfur, potassium, sodium, chlorine, iron and zinc. Again, these are harder to control to a threshold deficiency because algae generally require less of these nutrients.

In some embodiments, the growth inhibitive medium is deficient in one or more of nitrogen, phosphorus, calcium, magnesium, sulfur, potassium, sodium, chlorine, iron and zinc. In other embodiments, the growth-inhibitive medium is deficient in one or more of nitrogen and phosphorus. In other embodiments, the growth-inhibitive medium is deficient in one or more of calcium, magnesium, sulfur, potassium, sodium, chlorine, iron and zinc.

The growth-inhibitive medium could also include vitamins with positive effects on lipid synthesis. These vitamins include biotin, thiamine, and cobalamin. Not all algae need one or all of these vitamins. Some can synthesize their own—in a natural environment, phagotrophic algae can get the vitamins from the small microorganisms they ingest. If no small microorganisms are present, at least biotin (vitamin $B_7$) should be provided in the medium because biotin is the cofactor for a key enzyme involved in lipid synthesis.

The conditions of the growth-inhibitive medium and the algae, such as pH, temperature, and dissolved oxygen, can be adjusted to any conditions that will physiologically support the algae.

The pH should be controlled to physiological conditions for the algae. The pH can affect the ionic state/form of the chemicals added. For embodiments wherein organic acids are added, when pH is higher than the pKa values, the organic acids are present mostly as anions (negatively charged ions), and, when pH is lower than the pKa values, the organic acids are present mostly as neutral, uncharged, molecules. For embodiments wherein amines are added, when pH is higher than the pKa values of their conjugate acids, the amines are present mostly as neutral, uncharged, molecules, and, when pH is lower than the pKa values of their conjugate acids, the amines are present mostly as cations (positively charged ions). The transport of compounds is affected by the ionic state. If special active transport mechanisms are not involved, cell membranes in general are not permeable to ions but more permeable to small neutral molecules. Therefore, pH can affect the transport/uptake of the chemicals by algae and other microorganisms. In general, the pH should be maintained within the physiologically acceptable range and at values that give higher percentages of neutral molecules of the added chemicals (organic acids or amines) for more effective uptake by the algae.

The pH can be controlled by any means known in the art. In one or more embodiments, the pH of the growth-inhibitive medium is controlled by addition of aqueous acid solution(s) or aqueous base solution(s). In other embodiments, the pH of the growth-inhibitive medium can be maintained in the acceptable range with the use of pH buffers. The choice of pH buffers suitable for biological systems is known to those of ordinary skill in the art.

In one or more embodiments, the growth-inhibitive medium is at a pH of from 2.5 or more to 8 or less, in other embodiments, from 3 or more to 7.5 or less, and in still other embodiments, from 4 or more to 7 or less. In one or more embodiments, the growth-inhibitive medium is at a pH of 4 or more. In one or more embodiments, the growth-inhibitive medium is at a pH of 7 or less.

The temperature of the growth-inhibitive medium should be controlled to physiological conditions for the algae. The temperature can be controlled by any heating or cooling equipment as known in the art. Such equipment may employ temperature sensors, thermometers, thermocouples and the like to monitor temperature, further including heating and/or cooling elements to control the temperature of the medium as monitored by those elements. Cooling is normally achieved by running cold water or other fluids through tubes or plates that are in contact with the medium. Heating is often achieved either by running hot water or other fluids through tubes or plates that are in contact with the medium, or by using electrically heated tubes, plates or other surfaces.

In one or more embodiments, the growth-inhibitive medium is maintained at from 0° C. or more to 50° C. or less, in other embodiments, from 10° C. or more to 40° C. or less, and in still other embodiments, from 10° C. or more to 30° C. or less. In one or more embodiments, the growth-inhibitive medium is at a temperature of 20° C. or more. In one or more embodiments, the growth-inhibitive medium is at a temperature of 30° C. or less. It should be noted that different algae have different physiologically suitable and tolerable temperatures. The optimal temperatures may be adjusted if more thermophilic or more psychrophilic algae are used.

The dissolved oxygen content of the growth-inhibitive medium should be controlled to physiological conditions for the algae. The dissolved oxygen content can be controlled by any means known in the art. In one or more embodiments, the dissolved oxygen content of the growth-inhibitive medium is controlled by adjusting the aeration flow rate and/or oxygen partial pressure of the gas (air, pure oxygen or mixtures of air and oxygen) and/or by adjusting the speed of mechanical agitation. The aeration rate and agitation speed are maintained within the range that provides adequate medium mixing without damaging or killing the algae cells (due to high shear stress or other damaging mechanisms).

In one or more embodiments, the growth-inhibitive medium has a dissolved oxygen content of from 0.09 milligram per liter (mg/L) or more to 27.3 mg/L or less, in other embodiments, from 0.45 mg/L or more to 9.1 mg/L or less, and in still other embodiments, from 0.91 mg/L or more to 9.1 mg/L or less. In one or more embodiments, the growth-inhibitive medium has a dissolved oxygen content of 0.45 mg/L or more. In one or more embodiments, the growth-inhibitive medium has a dissolved oxygen content of 9.1 mg/L or less.

The algae take in nutrients and the lipid-precipitating addition and, if employed, the organic acid addition, through osmotrophy or phagotrophy or a combination thereof and thus the algae may be selected from osmotrophic algae and phagotrophic algae and mixtures thereof.

Osmotrophic algae are here defined as algae that uptake dissolved compounds through a membrane via not only osmosis but also other active transport mechanisms (excluding phagotrophy) across the membrane. Suitable osmotrophic algae may be chosen from *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora sp., Anabaena, Ankistrodesmus, Ankistrodesmus falcatus, Boekelovia hooglandii, Borodinella sp., Botryococcus braunii, Botryococcus sudeticus, Carteria, Chaetoceros gracilis, Chaetoceros muelleri, Chaetoceros muelleri subsalsum, Chaetoceros sp., Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora, Chlorella luteoviridis, Chlorella luteoviridis var. aureoviridis, Chlorella luteoviridis var. lutescens, Chlorella miniata, Chlorella minutissima, Chlorella mutabilis, Chlorella nocturna, Chlorella parva, Chlorella photophila, Chlorella pringsheimii, Chlorella Protothecoides, Chlorella protothecoides var. acidicola, Chlorella regularis, Chlorella regularis var. minima, Chlorella regularis var. umbricata, Chlorella reisiglii, Chlorella saccharophila, Chlorella saccharophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris, Chlorella vulgaris f. tertia, Chlorella vulgaris var. autotrophica, Chlorella vulgaris var. viridis, Chlorella vulgaris var. vulgaris, Chlorella vulgaris var. vulgaris f. tertia, Chlorella vulgaris var. vulgaris f. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Cryptomonas sp., Cyclotella cryptica, Cyclotella meneghiniana, Cyclotella sp., Dunaliella sp., Dunaliella bardawil, Dunaliella biocculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena, Franceia sp., Fragilaria crotonensis, Fragi-*

*laria* sp., *Gleocapsa* sp., *Gloeothamnion* sp., *Hymenomonas* sp., *Isochrysis* aff. *galbana*, *Isochrysis galbana*, *Lepocinclis*, *Micractinium*, *Micractinium*, *Monoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Pascheria acidophila*, *Pavlova* sp., *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pyramimonas* sp., *Pyrobotrys*, *Sarcinoid chrysophyte*, *Scenedesmus armatus*, *Spirogyra*, *Spirulina platensis*, *Stichococcus* sp., *Synechococcus* sp., *Tetraedron*, *Tetraselmis* sp., *Tetraselmis suecica*, *Thalassiosira weissflogii*, and *Viridiella fridericiana*.

Phagotrophic algae are algae that feed by engulfing their food, similar to the function of a mouth. Suitable phagotrophic algae may be chosen from several chrysomonad genera including *Dinobryon, Chrysophaerella, Uroglena, Catenochrysis, Ochromonas, Chromulina*, and *Chrysococcus*; the prymnesiophyte *Chrysochromulina*; the coccolithophorid *Coccolithus pelagicus*; the xanthophyte *Chlorochromonas*, the chrysophytes *Phaeaster, Chrysamoeba*, and *Pedinella*; the dinoflagellate *Ceratium hirundinella* Muller; and *Cryptomonas ovata* Ehrenberg.

In some embodiments, the algae are selected from *Chlorella* and *Ochromonas* species. In some embodiments, the algae are *Ochromonas* species. In some embodiments, the algae are *Chlorella* species.

As used herein, a lipid-precipitating addition is any addition that ultimately results in algae having a high concentration of lipids contained therein. In one or more embodiments, the lipid-precipitating addition is selected from hydroxyl-containing compounds and amine-containing compounds and mixtures thereof. In some embodiments, the lipid-precipitating addition is one or more hydroxyl-containing compounds. In one or more embodiments, the lipid-precipitating addition is one or more amine-containing compounds.

A hydroxyl-containing compound is any compound containing one or more hydroxyl groups. A hydroxyl group is a chemical functional group containing an oxygen atom connected to a hydrogen atom.

The hydroxyl-containing compound can generally be any alcohol. The hydroxyl-containing compound may be chosen from alcohols of different hydrocarbon chain lengths, different levels of saturation (i.e., without and with different percentages of double and triple bonds), and different additional functional groups such as ketone, ester, ether, carboxyl, amine, amide, sulfhydryl, sulfate, phosphate.

The hydroxyl-containing compound may be selected from the group consisting of glycerol, ethanol, methanol, propanol, butanol and mixtures thereof. Fatty alcohols of longer chains can also be used but, for economical purpose, may be introduced as mixtures derived from natural fats and oils.

For osmotrophic algae, the suitable choices are molecules that can be transported across the cell membrane by passive diffusion or by active transport mechanisms excluding phagotrophy. These molecules may be chosen from, for example, glycerol, methanol, ethanol, dihydroxyethane, propanol, isopropanol, cyclopropanol, propylene glycol, butanol, isobutanol, cyclobutanol, dihydroxybutanes, trihydroxybutanal, cyclohexanol, dihydroxycyclohexanes, phenol, dihydroxybenzenes, and trihydroxybenzenes.

For phagotrophic algae, in addition to the molecules mentioned above, hydroxyl-containing compounds can be dissolved molecules, colloidal molecules, or insoluble particles or droplets. An exception to this group is solid particles with sizes equal to or larger than the sizes of algae cells used, as the phagotrophic algae must be able to ingest the particle. In one or more embodiments, the hydroxyl-containing compound is selected from peptides, proteins, carbohydrates, polysaccharides, and derivatives and mixtures thereof. In one or more embodiments, the hydroxyl-containing compound may be a mixture of fatty alcohols derived from natural fats and oils, including waste oils.

In one or more embodiments, the hydroxyl-containing compound is maintained at a concentration of from 0.1 grams per liter (g/L) or more to 50 g/L or less in the growth-inhibitive medium. In other embodiments, the hydroxyl-containing compound is maintained at a concentration of from 0.5 g/L or more to 20 g/L or less, and in still other embodiments, from 1 g/L or more to 10 g/L or less, based upon algal concentration. In one or more embodiments, a hydroxyl-containing compound is at a concentration of 1 g/L or more, based upon algal concentration. In one or more embodiments, a hydroxyl-containing compound is at a concentration of 10 g/L or less, based upon algal concentration. It should be noted that depending on chain length and presence of other functional groups, the alcohols have widely varying solubility in water. The concentration used can be adjusted according to the potential negative effects of high concentrations on algae cells and according to whether an osmotrophic or phagotrophic alga is used; the former can only uptake dissolved alcohols while the latter can engulf fine droplets of insoluble fatty alcohols in addition to dissolved alcohols.

An amine-containing compound is any compound containing one or more amine groups. For the purpose of this invention, an amine group is any functional group that contains a basic nitrogen atom with at least one directly linked hydrogen atom.

The amine-containing compound may be chosen from any amine and amide with different molecular sizes and other potential functional groups present. For osmotrophic algae the suitable choices are molecules that can be transported across the cell membrane by passive diffusion or by active transport mechanisms, excluding phagotrophy. These smaller molecules may be chosen from, for example, ammonia, methylamine, dimethylamine, ethanolamine, methylethanolamine, aniline, diphenylamine, amino acids, peptides, biogenic amines (such as histamine), urea, acetamide, and other cyclic secondary amines and amides. For phagotrophic algae, in addition to the molecules mentioned above, amine-containing and amide-containing materials that are dissolved, colloidal, or insoluble can be used, with the exception of solid particles with sizes equal to or larger than the sizes of algae cells used. These molecules can have complex and various structures. In some embodiments, the amine-containing compound is selected from peptides, proteins, nucleic acids, and derivatives thereof and mixtures of the forgoing.

The amine-containing compounds are complex and have widely varying inhibitory concentrations to cells. Amino acids, peptides, proteins and nucleic acids are common nutrients and/or metabolites of cells and can generally be used in relatively high concentrations without inhibitory concerns. Other amine- and amide-based chemicals are harmful to cells, due to their basicity or solvent or surfactant properties, at certain critical concentrations. These compounds, when used, need to be continuously or step-wise added to maintain the concentrations below these inhibitory concentrations.

In some embodiments, an organic acid addition is added to the growth inhibitive medium in addition to the lipid-precipitation addition. In some embodiments, all three are added.

The organic acid addition is an addition of compounds containing carboxylic acid functional groups. In some embodiments the compounds are selected from organic acids, salts of organic acids and mixtures thereof. In some embodiments, the organic acid addition is chosen from short- and long-chain carboxylic acids, amino acids, sugar acids, peptides, proteins, waste oils, nucleic acids, carboxyl-containing polysaccharides, and various other carboxyl-containing materials.

In some embodiments, the organic acid addition is a waste oils selected from grease, waste cooking oil, waste processing oil, waste machinery oil, crude oil sludge, petroleum refinery oil sludge, biodiesel waste oil stream, and oil and grease collected from municipal and industrial wastewater.

The compounds of the organic acid addition can be small (C2 to C7) or large (C8 or larger). With larger organic acid additions, phagotrophic algae will be used, as the larger compounds cannot be readily taken in through osmotrophy. The larger compounds may be soluble, colloidal, or insoluble material consumable by the phagotrophic alga. The smaller compounds are appropriate for both phagotrophic and osmotrophic algae.

In some embodiments, the smaller compounds are selected from acetic acid, propanoic acid, isopropanoic acid, butanoic acid, isobutanoic acid, pyruvic acid, citric acid, isocitric acid, fumaric acid, malic acid, oxaloacetic acid, succinic acid, malonic acid, ketoglutaric acid, cyclopentanoic acid, cyclohexanoic acid, benzoic acid, and phenol-carboxylic acids.

In some embodiments, the organic acid has chain lengths of from C2 to C7. In some embodiments, the organic acids have chain lengths of from C7 to C24. For osmotrophic algae, it is beneficial or often necessary to use the smaller molecules of organic acids (C2 to C7) so that the molecules can be transported through cell membranes without involvement of any active transport mechanisms. For phagotrophic algae, in addition to the smaller molecules, larger molecules (C8 and larger), in dissolved, colloidal or solid state, can be used.

Short-chain organic acids have higher solubility in water and can be harmful to cells at concentrations beyond certain critical levels, due to acidity and/or solvent/surfactant properties. Different algae have different tolerance thresholds for different compounds. Longer-chain organic/fatty acids, without multiple functional groups, have low solubility in water. They tend to be present as a separate liquid or solid phase and can be used at higher concentrations with less concern about strongly harmful effects on cells. But only phagotrophic algae can effectively transport, by engulfing, these large organic acids into the cells. To break these larger compounds to smaller components that can be transported across the cell membrane, osmotrophic algae need to produce and employ extracellular enzymes.

In one or more embodiments, the organic acid addition is maintained at a concentration of from 0.01 g/L or more to 50 g/L or less in the growth-inhibitive medium. In other embodiments, the organic acid addition is maintained at a concentration of from 0.1 g/L or more to 20 g/L or less, and still other embodiments, from 0.5 g/L or more to 10 g/L or less, based upon algal concentration. In one or more embodiments, a organic acid addition is at a concentration of 0.5 g/L or more, based upon algal concentration. In one or more embodiments, a organic acid addition is at a concentration of 5 g/L or less, based upon algal concentration.

Organic acids having carbon chains of C6 or shorter are generally soluble in water and can therefore generally transfer across algae membrane, through osmotrophy. Organic acids having carbon chains of C7 or longer are generally insoluble in water. For transport in high rates, these insoluble droplets or particles of longer-chain organic acids have to be taken into algae by phagotrophy. Without being bound to any theories, it is hypothesized that the effect of organic acid addition is catalyzed or otherwise affected by the algae's enzymes, resulting in the algae storing insoluble lipids inside the cells of the algae. Different algae will produce different lipid chain lengths, but the theory is that the algae uptake the smaller organic acid additions and produce organic acids with larger chain length.

Some algae, such as *Ochromonas* species and *Chlorella* species have been found to produce lipids with chain lengths of C18 and C20 under normal conditions. The organic acids may not propagate to such long chain lengths under stressed conditions or in presence of high concentrations of shorter-chain organic acids. With the addition of hydroxyl-containing compounds or amine-containing compounds, the carboxyl group of the produced organic acid further reacts with the hydroxyl group of hydroxyl-containing compounds or the amine group of amine-containing compounds and produce ester or amide. The produced ester or amide is less soluble in water and precipitates out of solution in the form of lipid particles at lower concentrations. These reaction and precipitation actions are hypothesized to eliminate the harmful acidity associated with the organic acids and reduce the soluble concentrations of these compounds.

The essential nutrients concentration within the algae medium is monitored to ensure that the medium is a growth-inhibitive medium. The lipid precipitating addition can be added to the growth-inhibitive medium before or after or at the same time as adding organic acid.

For economical purpose, chemicals added in the process should not be wasted. Thus, in some embodiments, the algae concentration in the growth-inhibitive medium (say 10 g/L) and the initial lipid content already in the algae (say 20%) are first determined. There after a target desired intracellular lipid content is established (say 70%). Preliminary experiments are conducted to determine the conversions of lipid-precipitating addition and, if employed, organic acid addition, to intracellular lipids (say, 60% for organic acid and 80% for lipid-precipitating addition) and to also determine the optimal ratio of organic acid to precipitating-addition for lipid formation (say 10:1). Then, the total amounts of organic acid and lipid-precipitating addition that should be added can be determined from material balance calculation.

For the above example numbers, the lipid and non-lipid amounts in the initial algae are 2 (=10×20%) and 8 g/L, respectively. For intracellular lipids to reach 70%, the 8 g/L non-lipid materials correspond to 30% of the total weight of the final algae; thus, the total weight is 26.7 (=8/0.3) g/L and the lipid weight is 18.7 (=26.7−8) g/L. So, the increase of lipid amount required is 16.7 (=18.7−2) g/L. To achieve that lipid amount increase, we need to add 2.45 g/L precipitating-addition and 24.5 g/L organic acid, according to the above given optimal ratio and conversions. If these amounts are within the tolerance levels of those compounds, without causing damages to cells, they can be considered to be added in one time; otherwise, they need to be slowly added with control, continuously or step-wise, to keep the concentrations at any time to be lower than their threshold levels.

After production of high lipid content algae in accordance with this invention, the lipids may be extracted and reacted with alcohols through well-known chemical processes to make biodiesel, i.e., methyl or ethyl esters of fatty acids.

In a specific embodiment, the growth-inhibitive medium is deionized water that can have salts or vitamins (particularly biotin) for maintaining suitable osmotic pressure, pH buffer effect, or activities of enzymes involved in lipid synthesis, the growth-inhibitive medium is deficient in nitrogen and phosphorus, the algae are *Ochromonas danica*, and the lipid-precipitating addition is hydroxyl-group containing compounds.

In another specific embodiment, the growth-inhibitive medium is deionized water that can have salts or vitamins (particularly biotin) for maintaining suitable osmotic pressure, pH buffer effect, or activities of enzymes involved in lipid synthesis, the growth-inhibitive medium is deficient in nitrogen and phosphorus, the algae are *Ochromonas danica*, and the lipid-precipitating addition is amine-group containing compounds.

In another specific embodiment, the growth-inhibitive medium is phosphorus salts and deionized water that can have salts or vitamins (particularly biotin) for maintaining suitable osmotic pressure, pH buffer effect, or activities of enzymes involved in lipid synthesis, the growth-inhibitive medium is deficient in nitrogen, the algae is *Ochromonas danica*, the lipid-precipitating addition is hydroxyl-containing compounds, and the organic acid addition is acetic acid.

In another specific embodiment, the growth-inhibitive medium is provided as broadly described herein, the lipid-precipitating addition is glycerol and the organic acid is acetic acid or other carboxylic acids, and the algae produces glycerides as the desirable high lipid content and intracellular lipid particles. For biodiesel production, the lipids are extracted from the algae and reacted with alcohols, such as methanol or ethanol, through well-known chemical processes to make biodiesel. The glycerol in the glycerides does not end up in the biodiesel. It becomes a waste or byproduct, to be recycled and reused as the lipid-precipitation addition.

In particular embodiments, the alcohols typically employed to create biodiesel through reaction with the extracted lipids form at least a portion of the lipid-precipitating addition. When alcohols such as methanol and ethanol are added to the growth-inhibitive medium together with an organic acid addition as taught herein, the algae utilize the hydroxyl group of the small chain alcohol to neutralize the accumulated free fatty acid inside the algal cell and produce methyl ester, which can be directly used as biodiesel without any transesterification or esterification. In these embodiments, the esters of the fatty acids are considered to be a lipid. It is theorized that the algal enzymes catalyze an esterification of the hydroxyl groups in alcohols (methanol and ethanol) and the carboxylic acid groups (of the organic acid addition), and make the biodiesel directly inside the algae cells. Thus, the post-extraction reaction to form biodiesel will no longer be needed, and the typically recycled alcohol (glycerol in the above example) need not be used and thus not reused or recycled.

In particular embodiments, the method includes the direct formation of biodiesel by algae. In some such embodiments, the lipid-precipitating addition is selected from the group consisting of methanol, ethanol, propanol, isopropanol, and mixtures thereof. In some such embodiments, the organic acid addition is selected from the group consisting of acetic acid, citric acid, natural oils, natural fats, waste oils, waste fats, fatty acids derived from this group, and mixtures thereof.

It will be appreciated that larger alcohols (greater chain lengths than those listed above) might be used in instances where the algae produce relatively shorter chain lengths from the carboxylic acids synthesized by the cells. Methyl esters are currently popular as biodiesel such that methanol will be particularly useful. The real limitation is that the final esters' chain lengths are not longer than C22-C24, because they are no longer liquid fuels.

In light of the foregoing, it should be appreciated that the present invention significantly advances the art by providing methods for the production of algae having high lipid content. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Experiment 1: Algae Culture with Bacteria and Ketchup as Carbon Source

The objective of Experiment 1 was to investigate algae culture using bacteria and ketchup as the carbon source. The algal growth and lipid production were measured.

1.8 g/L bacteria cell were added to mineral solution and then a small amount of algae were inoculated into the bacteria solution for batch culture. During the batch studies, the pH of all systems was maintained at 5 with 0.2 mol/L NaOH and 0.2 mol/L HCl.

Algae were cultured in a 3 L fermentor at 200 rpm with 5% dissolved oxygen by waste ketchup sugar and nitrogen source ($NH_4Cl$ and yeast extract). The initial pH was uncontrolled until it dropped back and was maintained at 5 by 1 mol/L HCl. Algae were then fed by additional ketchup sugar and a nitrogen source to grow to high concentration.

The material used included mineral solutions (0.13 g/L $KH_2PO_4$, 0.3 g/L $MgSO_4.7H_2O$, 0.18 g/L $CaCl_2.2H_2O$, 0.01 g/L $MgCl_2.4H_2O$, and 5 g/L NaCl), glucose, ketchup sugar, yeast extract, $NH_4Cl$, NaOH, and HCl.

For the dry weight analysis, algal cells were collected by centrifuging at 300 g for 10 min. After washing with deionized water once, the precipitant of the sample was transferred to pre-weighed aluminum plates and dried to a constant weight in an oven at 70 degrees C.

For the lipid analysis, the algal cells were collected at 300 g for 10 min. Then the lipid content of the precipitant from the sample was analyzed with the same lipid extraction procedure, which is modified from the Folch method. The specific procedure was:

i. Add 8 mL of chloroform and methanol mixture (2:1, v/v) to the sample
ii. Add 0.1 mL of HCl (5 M) to the sample
iii. Gradually add deionized water to the sample until a second phase appears
iv. Vortex for 3 min at full power (Vortex-Genie 2)
v. Rotate 20 min at 40% output (Glas-Col)
vi. Centrifuge at 3620 g for 5 min
vii. Collect the lower chloroform phase into a pre-weighed drying vessel viii. Add 5 mL of chloroform and methanol mixture (2:1, v/v) to the sample and repeat steps iv, v, vi and vii
ix. Air dry the vessel to a constant weight and measure the weight.

For the algae concentration analysis, the algal sample was first fixed with an equal volume of 2% glutaraldehyde solution, and then the number concentration were determined by using a Petroff-Hausser counting chamber (Catalog #3900, Cell-Depth: 0.02 mm, Ruling Pattern: Improved Neubauer, 1/400 square mm) under microscope.

With *E. coli* as the only nutrients source, alga doubling time varied from 12 hrs to 20 hrs according to different pHs, illuminations, initial substrate volumes, etc in bacteria medium (FIG. 1). Alga dry weight yield varied from 26% to 40%. The lipid contents varied from 29% to 37%. FIG. 1 shows alga growth profiles with *E. coli* as the nutrient source.

Figure 2:
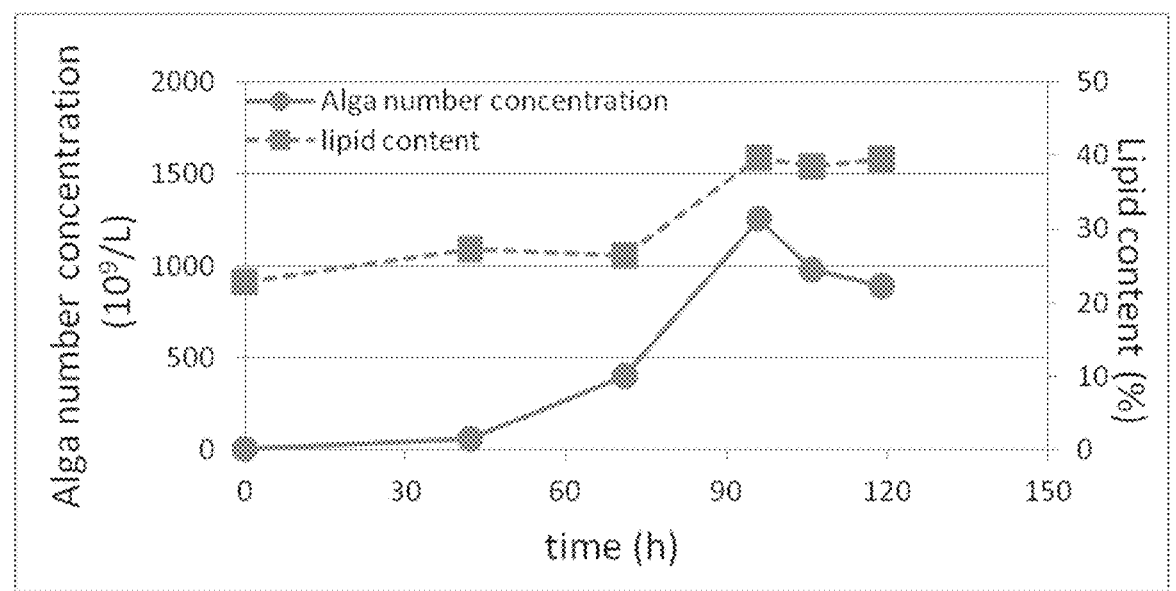
FIG. 2 is a graph showing alga growth profiles with ketchup as the carbon source.

With commercial ketchup as carbon source and ammonia as nitrogen source, alga doubling times varied from 9 hrs to 13 hrs according to different environment (FIG. 2). Alga dry weight yield varied from 27% to 38%. The lipid contents varied from 33% to 46%. FIG. 2 shows alga growth profiles with ketchup as the carbon source.

Experiment 2: Lipid Enhancement with Acetic Acid/Acetate Salts

The objective of Experiment 2 was to investigate the effect of acetic acid and sodium acetate on lipid enhancement.

The acetic acid molecules were formed into acetyl-CoA and the acetyl-CoA was further processed into free fatty acid. Compared to the conversion of glucose into free fatty acid, the conversion of acetic acid into free fatty acid requires less steps and enzyme, which makes it more effective in enhancing lipid production.

Algae were first cultured and then collected by centrifuge. After washing with deionized water once, algae were re-suspended into salts solution (Table 1). 0.5, 1, and 1.5 g/L sodium acetate were added to the re-suspended algae solution individually at the beginning. During the batch studies, the pH of all systems was maintained at 5 with 0.05 mol/L NaOH and 0.05 mol/L HCl.

TABLE 1

Salts solution for fattening studies.

| Salt | Concentration (g/L) |
| --- | --- |
| $KH_2PO_4$ | 0.3 |
| $MgCO_3$ | 0.4 |
| $CaCO_3$ | 0.05 |
| $MgSO_4$ 7H2O | 0.1 |
| $Na_2EDTA$ | 0.0044 |
| $H_3BO_3$ | 0.00097 |
| $FeCl_3$ 6H2O | 0.00315 |
| $MnCl_2$ 4H2O | 0.00018 |
| $ZnSO_4$ 7H2O | 0.00002 |
| $CoCl_2$ 6H2O | 0.00001 |
| $Na_2MoO_4$ 2H2O | 0.000006 |

The materials used in Experiment 2 were salt solution (Table 1), sodium acetate, NaOH, HCl, chloroform, methanol, acetic acid, hexane, diethyl ether, and acetone.

The dry weight analysis and lipid analysis were performed the same as in Experiment 1.

For thin layer chromatography analysis (TLC) First the TLC plates (PN #5721-7, EMD) were run to 5 cm from the bottom in Chloroform-methanol-acetic acid (90:10:1, v/v/v). After drying, the plates were run in hexane-diethyl ether-acetone (60:40:5, v/v/v) to 16 cm. Again, the plates were dried and then run in hexane-diethyl ether (97:3, v/v) to 19 cm.

Figure 3:
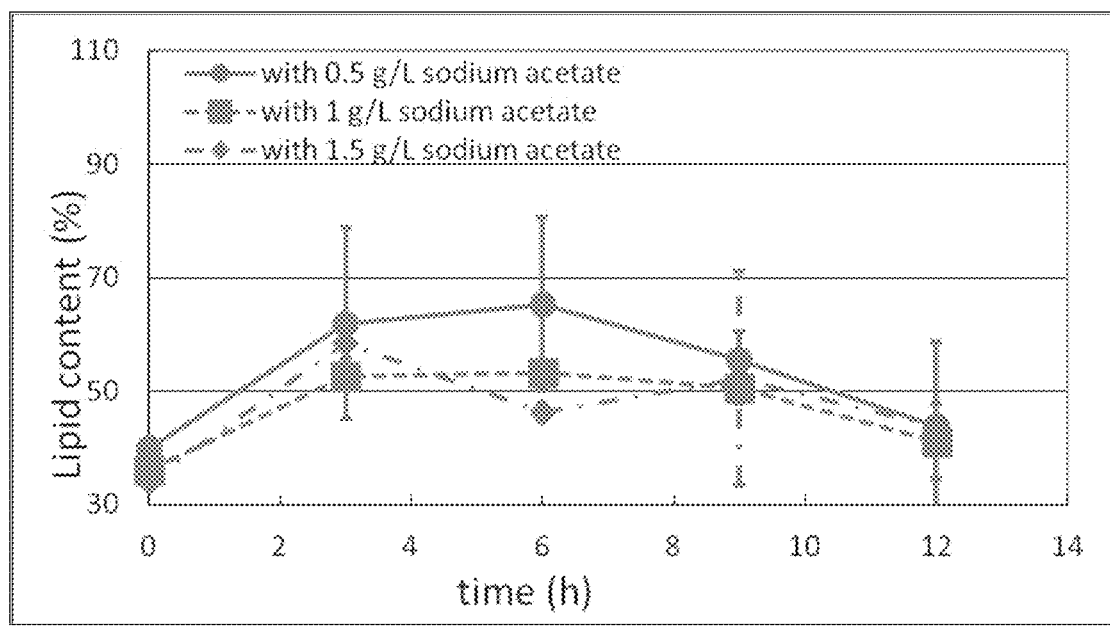
FIG. 3 is a graph showing the lipid content change with time with sodium acetate as the only carbon source.

In the system with 0.5 g/L sodium acetate, the lipid content first increased from 40% of the dry weight to 65% of the dry weight within 6 hours (FIG. 3). And then the lipid content began to decrease. The lipid content change of the systems with 1 and 1.5 g/L sodium acetate shows the similar trend. TLC analyses demonstrated the lipid profile of the system with 0.5 g/L sodium acetate at 0 and 6 h. The increase of lipid is mainly due to the increase of free fatty acid. FIG. 3 shows the lipid content change with time with sodium acetate as the only carbon source. Through TLC, lipid profiles were obtained for various systems including: lipid profile with glucose as the carbon source; the lipid profile with sodium acetate as the carbon source; and lipid profile with glycerol as the carbon source.

These results demonstrate that acetic acid/acetate salts can be utilized by algae to produce free fatty acid and hence increase the total lipid content. However, when the free fatty acid concentration inside the algal cell reaches a certain level, the algae are inhibited by the free fatty acid and the lipid content started to decrease.

Experiment 3: Lipid Enhancement with Glycerol

Glycerol molecules have three hydroxyl groups, which can react with the carboxyl group of free fatty acid to form triglyceride. Triglyceride have no inhibitory effect on organism cells and thus the inhibitory effect of free fatty acid can be prevented by converting the free fatty acid to neutral triglyceride and the lipid content can be further enhanced.

Algae were first cultured and then collected by centrifuge. After washing with deionized water once, algae were re-suspended into salts solution (Table 1). 0.5, 1, and 5 g/L glycerol were added to the re-suspended algae solution individually at the beginning. During the batch studies, the pH of all systems was maintained at 5 with 0.05 mol/L NaOH and 0.05 mol/L HCl.

The materials used in Experiment 3 were salt solution (Table 1), glycerol, NaOH, HCl, chloroform, methanol, acetic acid, hexane, diethyl ether, and acetone.

The dry weight analysis and lipid analysis were performed the same as in Experiment 1. The thin layer chromatography analysis was performed the same as in Experiment 2.

Figure 4:
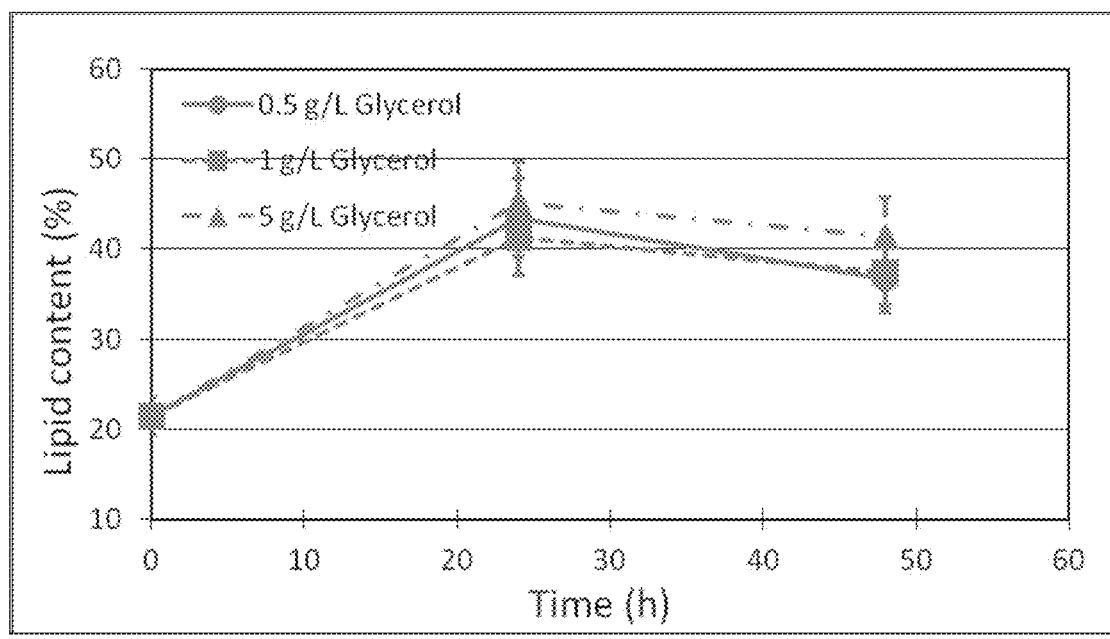
FIG. 4 is a graph showing the lipid profile with different concentrations of glycerol as carbon source.

In all the systems, the lipid content increased to about 40% of the dry weight within 24 h and then decreased slightly (FIG. 4). The concentration of glycerol has no obvious effect on the lipid content. TLC analysis demonstrate that the free fatty acid part reduced and the triglyceride part became larger compared to the initial algae culture. FIG. 4 shows the lipid profile with different concentrations of glycerol as carbon source.

These results show that glycerol can convert the free fatty acid part of algal lipid into triglyceride. However, because the amount of free fatty acid inside the cultured algal cell is relatively low, the increase of lipid content was not obvious.

Experiment 4: Lipid Enhancement with Acetic Acid/Acetate Salts and Glycerol

The experiments with acetic acid/acetate salts show that the free fatty acid part of algal lipid can be enhanced by acetic acid, but the inhibitory effect of free fatty acid on algal cell prevents further lipid enhancement. The studies with glycerol reveal that the glycerol can convert the free fatty acid part of algal lipid into triglyceride, but the conversion of free fatty acid into triglyceride slightly enhances the lipid production. Hence, by adding both acetic acid/acetate and glycerol, the free fatty acid produced from acetic acid can be converted to triglyceride by glycerol and high level of lipid is achievable.

Algae were first cultured and then collected by centrifuge. After washing with deionized water once, algae were re-suspended into salts solution (Table 1). 0.5 g/L glycerol was first added to the re-suspended algae solution and after 3 h, 1 g/L sodium acetate was pumped into the solution in 1 h. During the batch studies, the pH of all systems was maintained at 5 with 0.05 mol/L NaOH and 0.05 mol/L HCl.

The materials used in Experiment 4 were salt solution (Table 1), glycerol, sodium acetate, NaOH, and HCl.

The procedure, dry weight analysis, and lipid analysis were performed the same as in Experiment 1.

Figure 5:
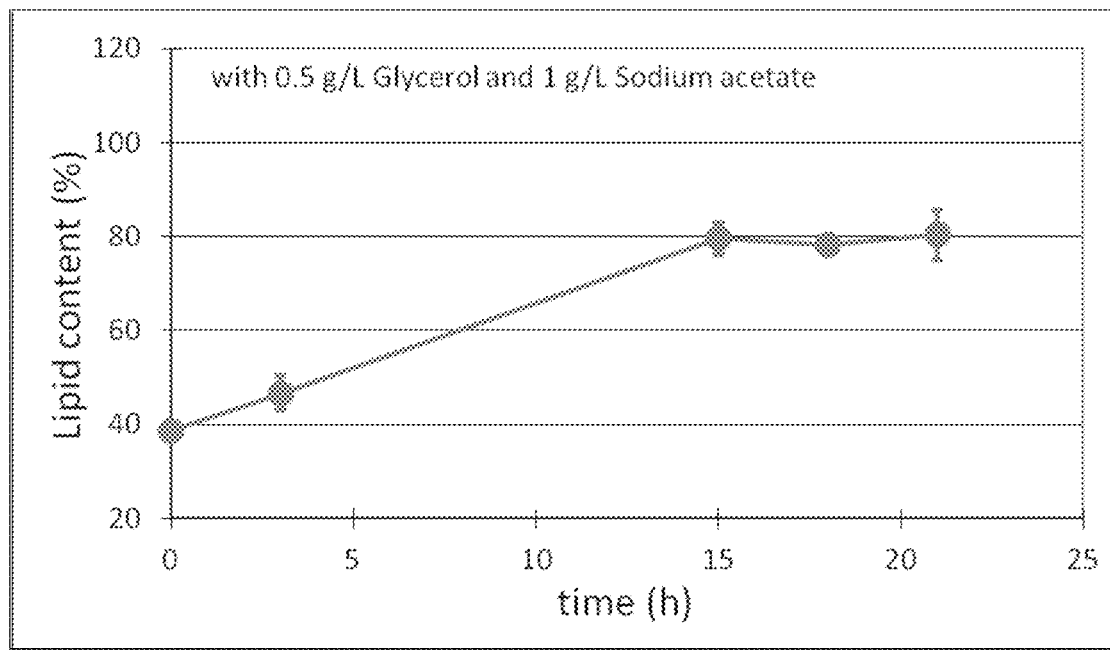
FIG. 5 is a graph showing the lipid profile with glycerol and sodium acetate as carbon sources.
Figure 6:
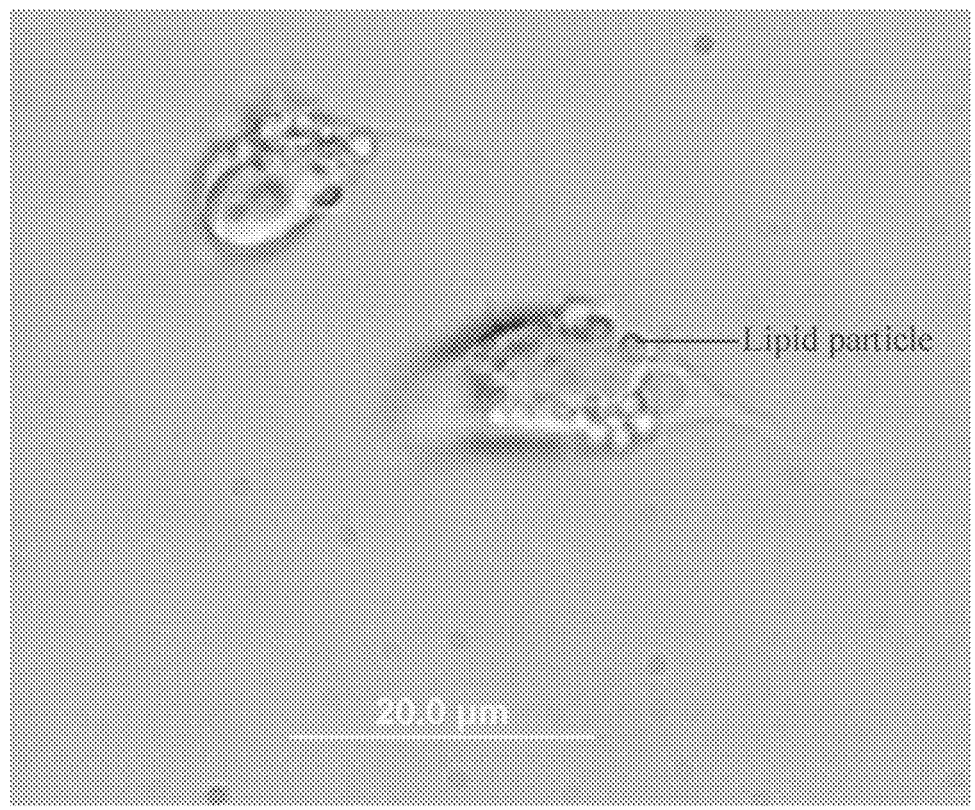
FIG. 6 is a microscopic image showing insoluble lipid particles inside algal cells.

The lipid content kept increasing from 40% of the dry weight to 80% of the dry weight within 15 h and then the lipid content kept constant at that value (FIG. 5). Microscopic images demonstrates that small particles inside alga cells were observed in 15 hrs after adding sodium acetate/glycerol (FIG. 6), while with glucose, bacteria, ketchup, sodium acetate or glycerol as the carbon source, no particles inside alga cells were observed. FIG. 5 shows the lipid profile with glycerol and sodium acetate as carbon sources. FIG. 6 shows microscopic images showing insoluble lipid particles inside algal cells.

These results demonstrate glycerol can convert the free fatty acid produced from acetic acid into triglyceride and form insoluble lipid particles. The formation of the insoluble lipid particles can avoid the inhibitory effect of free fatty acid and thus largely enhance the lipid productivity.

Experiment 5: Lipid Enhancement with Oleic Acid and Glycerol

Algae were first cultured and then collected by centrifuge. After washing with deionized water once, algae were re-suspended into salts solution (Table 1). 1 g/L of oleic acid were added to the re-suspended algae solution at the beginning, and after 5 h, 5 g/L of glycerol and 5 g/L of oleic acid were added to the algae solution. During the study, the pH of all system was maintained at 5 with 0.1 mol/L NaOH and 0.1 mol/L HCl.

The materials used in Experiment 5 were salt solution (Table 1), oleic acid, glycerol, NaOH, HCl, chloroform, methanol, acetic acid, hexane, diethyl ether, acetone.

For the dry weight analysis, algal cells were collected by centrifuging at 300 g for 10 min. After washing with deionized water once, the precipitant of the sample was transferred to pre-weighed aluminum plates and dried to a constant weight in an oven at 70 degrees C.

For the lipid analysis, the algal cells were collected at 300 g for 10 min. Then the lipid content of precipitant from sample was analyzed with a lipid extraction procedure, which is modified from the Folch method. The specific procedure was the same as steps i through ix from Experiment 1.

For the thin layer chromatography analysis (TLC), first the TLC plates (PN #5721-7, EMD) were run to 3 cm from the bottom in diethyl ether. After drying, the plates were run in hexane-diethyl ether-acetic acid (90:30:1, v/v/v) to 15 cm. Then, the plates were dried and dyed with primuline solution ((5 mg primuline in 100 ml of acetone/water, 80/20, v/v).

Figure 7:
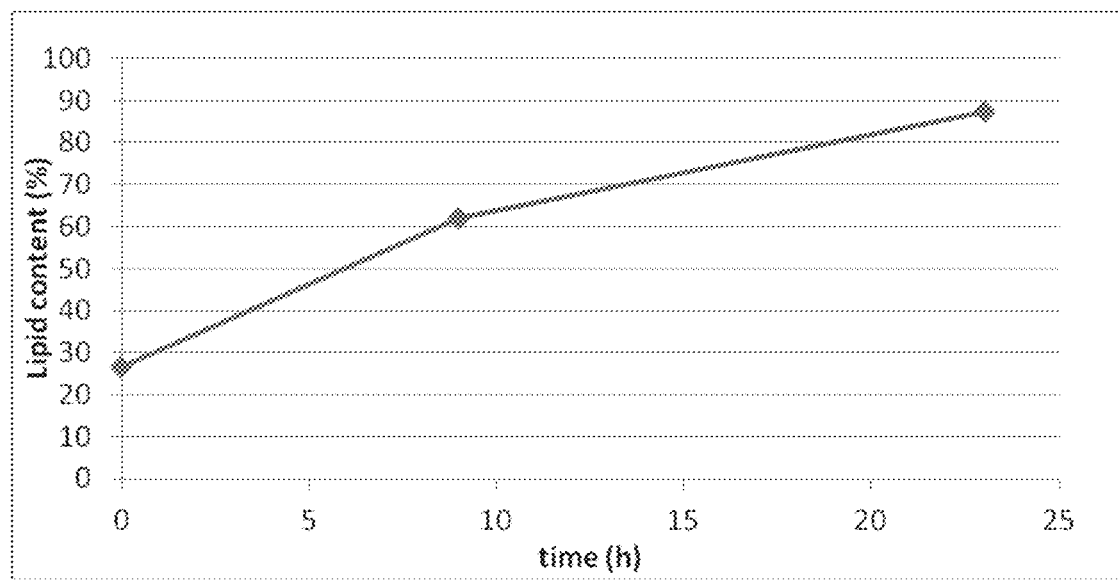
FIG. 7 is a graph showing the lipid content change with time with oleic acid and glycerol as the only carbon source.

At 0 h, the lipid content was about 26.6% of dry weight. After 9 h, the lipid content was increased to 61.9% (FIG. 7) and a TLC analysis showed the increase of the lipid is mainly due to the increase of the free fatty acid. After 23 h, the lipid content was further increased to 87.3% and the TLC analysis demonstrates that part of the free fatty acid accumulated inside algal cell was converted to triglycerides. FIG. 7 shows the lipid content change with time with oleic acid and glycerol as the only carbon source. TLC analysis (not shown) showed the lipid profile with oleic acid and glycerol as carbon sources.

These results demonstrate that algae can also use long-chain free fatty acid (oleic acid) to produce and accumulate lipid inside cell and glycerol can be utilized by the algae to convert the free fatty acid inside the cell into triglycerides.

Experiment 6: Lipid Enhancement with Oleic Acid and Methanol

Algae were first cultured and then collected by centrifuge. After washing with deionized water once, algae were re-suspended into salts solution (Table 1). 4.5 g/L of oleic acid was added to the re-suspended algae solution, and after 6 h, 0.8 g/L methanol were added to the algae solution. During the study, the pH of all systems was maintained at 5 with 0.1 mol/L NaOH and 0.1 mol/L HCl.

The materials used in Experiment 6 were salt solution (Table 1), oleic acid, methanol, NaOH, HCl, chloroform, methanol, acetic acid, hexane, diethyl ether, and acetone.

For the dry weight analysis, algal cells were collected by centrifuging at 300 g for 10 min. After washing with deionized water once, the precipitant of sample was transferred to pre-weighed aluminum plates and dried to constant weight in oven at 70 degrees C.

For the lipid analysis, the algal cells were collected at 300 g for 10 min. Then the lipid content of precipitant from the sample was analyzed with a lipid extraction procedure, which is modified from Folch method. The specific procedure was the same as steps i through ix from Experiment 1.

For the thin layer chromatography analysis (TLC), first the TLC plates (PN #5721-7, EMD) were run to 3 cm from the bottom in diethyl ether. After drying, the plates were run in hexane-diethyl ether-acetic acid (90:30:1, v/v/v) to 15 cm. Then, the plates were dried and dyed with primuline solution ((5 mg primuline in 100 ml of acetone/water, 80/20, v/v).

Figure 8:
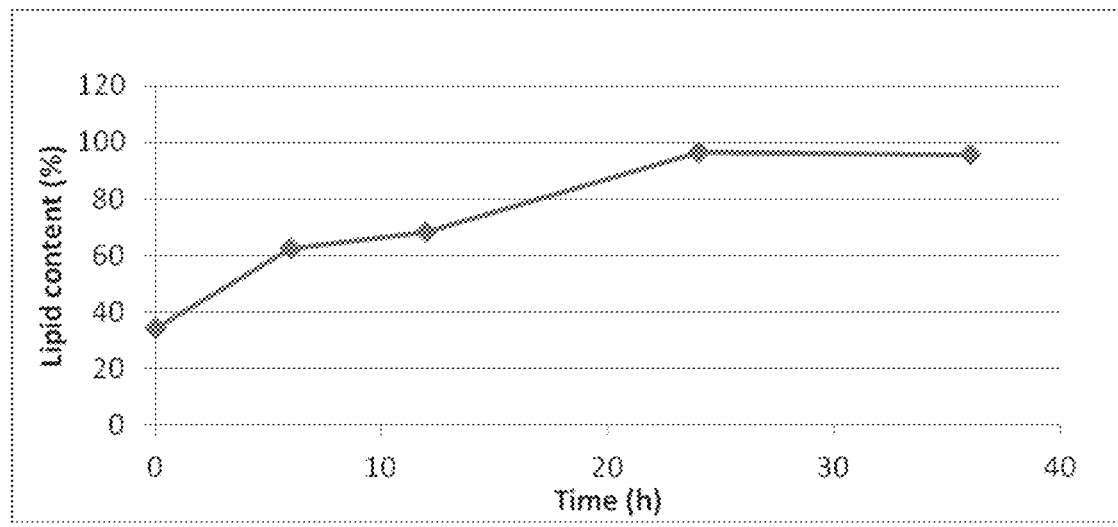
FIG. 8 is a graph showing the lipid content change with time with oleic acid and methanol as carbon sources.
Figure 9:
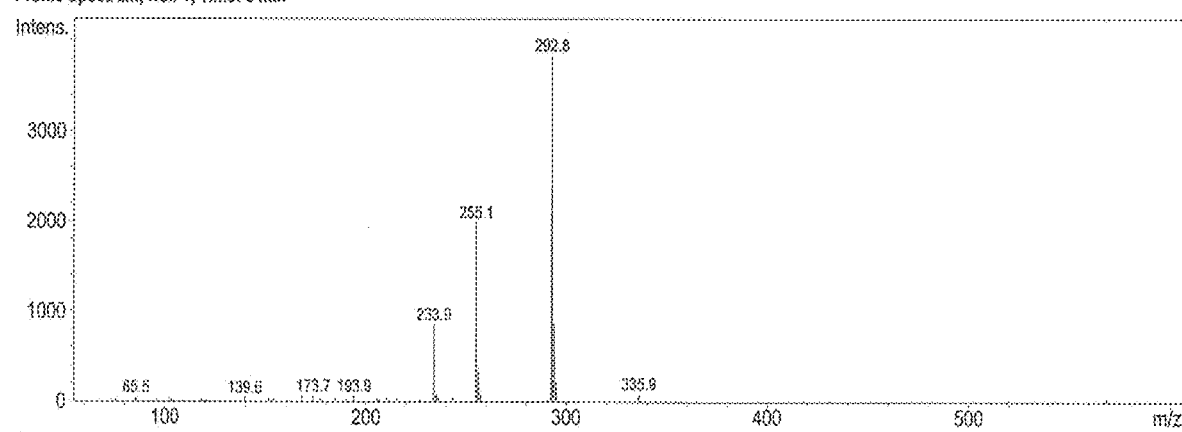
FIG. 9 is the mass spectrometer profile of a methyl oleate standard.
Figure 10:
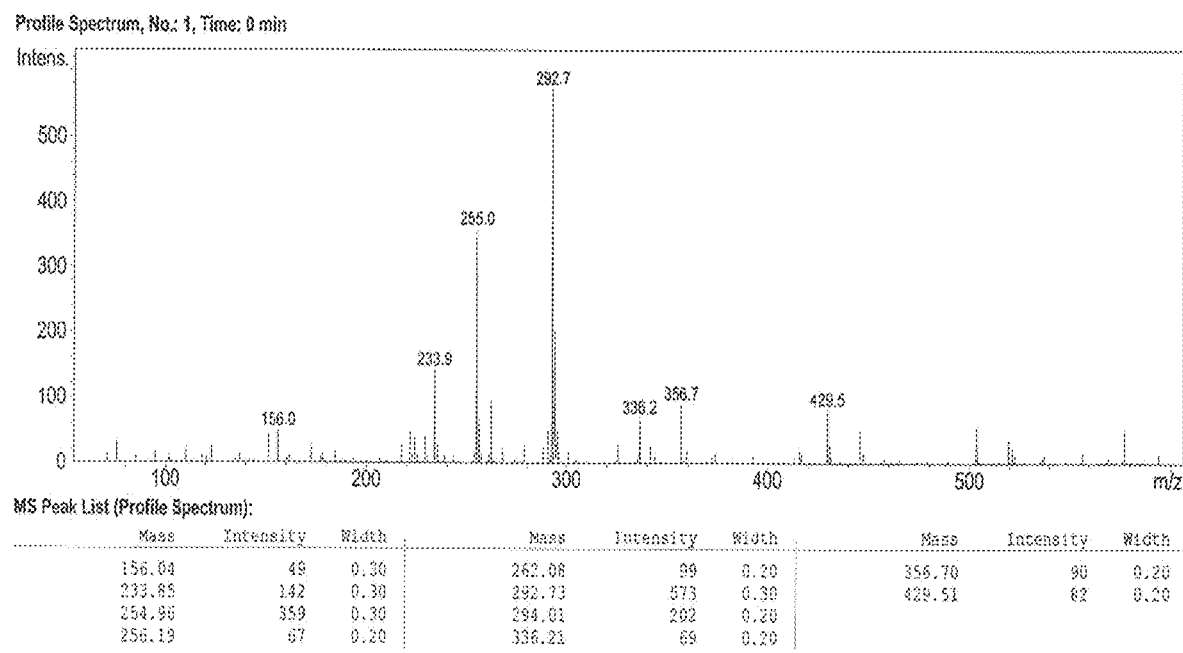
FIG. 10 is the mass spectrometer profile of a lipid sample of algae collected at 24 h.

At 0 h, the lipid content was about 34.5% of dry weight. After 6 h, the lipid content was increased to 62.2% (FIG. 8) and a TLC analysis showed the increase of the lipid is mainly due to the increase of the free fatty acid. After 24 h, the lipid content was further increased to 96.3% and the TLC and Mass Spectrometer (FIGS. 9 and 10) analysis demonstrate part of the free fatty acid accumulated inside algal cell was converted to methyl oleate. FIG. 8 shows lipid content change with time with oleic acid and methanol as carbon sources. FIG. 9 shows the mass spectrometer profile of a methyl oleate standard and FIG. 10 shows a lipid sample of algae collected at 24 h.

These results demonstrate that algae can also utilize the hydroxyl group of methanol to neutralize the accumulated free fatty acid inside algal cell and produce methyl ester, which can be directly used as biodiesel without any transesterification or esterification.

Various modifications and alterations that do not depart from the scope and spirit of this invention will become apparent to those skilled in the art. This invention is not to be duly limited to the illustrative embodiments set forth herein.

What is claimed is:

1. A method for increasing the lipid content of algae comprising the steps of
   providing a growth-inhibitive medium including algae, the algae having free fatty acid therein and being selected from the group consisting of phagotrophic algae and osmotrophic algae, wherein the growth-inhibitive medium is deficient in at least one nutrient that is necessary for reproductive growth of algae, thus frustrating algae reproduction, the at least one nutrient deficient in the growth-inhibitive medium being selected from the group consisting of nitrogen, phosphorus, magnesium, sulfur, and calcium, determining a concentration of the algae within the growth-inhibitive medium, establishing a target for a concentration of insoluble lipid to be produced within the algae, determining a ratio of a lipid-precipitating addition and an organic acid addition to be combined with the algae based on the established target for the concentration of insoluble lipid to be produced within the algae, after the step of determining the concentration and the step of establishing the target and the step of determining the ratio, combining the lipid-precipitating addition and the organic acid addition with the algae according to the determined ratio, wherein the lipid-precipitating addition is selected from hydroxyl-containing compounds and amine-containing compounds, wherein the hydroxyl-containing compounds are selected from the group consisting of glycerol, methanol, ethanol, dihydroxyethane, propanol, isopropanol, cyclopropanol, propylene glycol, butanol, isobutanol, cyclobutanol, dihydroxybutanes, trihydroxybutanal, cyclohexanol, dihydroxycyclohexanes, phenol, dihydroxybenzenes, and trihydroxybenzenes, and wherein the amine-containing compounds are selected from the group consisting of ammonia, methylamine, dimethylamine, ethanolamine, methylethanolamine, aniline, diphenylamine, amino acids, peptides, biogenic amines, urea, acetamide, cyclic secondary amines, and cyclic secondary amides, wherein the organic acid addition is a compound containing carboxylic acid functionality, the organic acid addition being provided at a concentration of from 0.5 g/L to 10 g/L, allowing the lipid-precipitating addition and the organic acid addition to be taken in by the algae, allowing the lipid-precipitating addition to react with the free fatty acid within the algae to thereby remove or reduce the self-regulation of lipid production by the algae, normally achieved by the free fatty acid, the reaction between the lipid-precipitating addition and the free fatty acid forming the insoluble lipid inside the algae, and extracting the insoluble lipid from the algae.

2. The method of claim 1, wherein the algae is selected from *Ochromonas* species.

3. The method of claim 1, wherein the lipid-precipitating addition is a hydroxyl-containing compound selected from the group consisting of glycerol, methanol, ethanol, dihydroxyethane, propanol, isopropanol, cyclopropanol, propylene glycol, butanol, isobutanol, cyclobutanol, dihydroxybutanes, trihydroxybutanal, cyclohexanol, dihydroxycyclohexanes, phenol, dihydroxybenzenes, and trihydroxybenzenes, the lipid-precipitating addition being provided at a concentration of from 1 g/L to 10 g/L.

4. The method of claim 1, wherein the lipid-precipitating addition is an amine-containing compound selected from the group consisting of ammonia, methylamine, dimethylamine, ethanolamine, methylethanolamine, aniline, and diphenylamine.

5. The method of claim 1, wherein the lipid-precipitating addition is an amine-containing compound selected from the group consisting of methylamine, dimethylamine, ethanolamine, methylethanolamine, aniline, diphenylamine, urea, acetamide, cyclic secondary amines, and cyclic secondary amides.

6. The method of claim 1, wherein the compound containing carboxylic acid functionality is selected from the group consisting of organic acids, salts of organic acids and mixtures thereof.

7. The method of claim 1, wherein the growth-inhibitive medium is water based.

8. The method of claim 1, wherein the growth-inhibitive medium is selected from distilled water, deionized water, tap water, river water, lake water, and sea water.

9. The method of claim 1, wherein the growth-inhibitive medium is a salt solution and includes one or more mineral salts.

10. The method of claim 9, wherein the one or more mineral salts is selected from the group consisting of ammonium chloride, potassium phosphate, magnesium sulfate, magnesium carbonate, calcium carbonate, sodium chloride, potassium chloride, ferric chloride, manganese chloride, manganese sulfate, copper sulfate, zinc sulfate, cobalt sulfate, boric acid, ammonium heptamolybdate, and sodium vanadate.

11. The method of claim 1, wherein the conditions of the growth-inhibitive medium and the algae are maintained at conditions that physiologically support the algae.

12. The method of claim 1, wherein the algae includes enzymes therein, the method further comprising the step of allowing the enzymes to catalyze the reaction of the lipid-precipitating addition with the free fatty acid.

13. The method of claim 1, wherein the insoluble lipid is present as numerous small particles inside the algae and not as one large combined particle.

14. The method of claim 1, wherein the insoluble lipid is present inside the algae at a concentration of 80% or more based on dry weight.

15. A method for increasing the lipid content of algae comprising the steps of providing algae having free fatty acid therein, the algae being selected from the group consisting of phagotrophic algae and osmotrophic algae, accumulating free fatty acid inside the algae, combining a lipid-precipitating addition and an organic acid addition with the algae in a growth-inhibitive medium, wherein the lipid-precipitating addition is selected from the group consisting of methanol and ethanol, wherein the organic acid addition is a compound containing carboxylic acid functionality, allowing the lipid-precipitating addition to be taken in by the algae, allowing the lipid-precipitating addition to react with the accumulated free fatty acid within the algae to thereby neutralize the accumulated free fatty acid with the hydroxyl group of the lipid-precipitating addition, to thereby remove or reduce the self-regulation of lipid production by the algae, normally achieved by the free fatty acid, the reaction between the lipid-precipitating addition and the free fatty acid forming an insoluble lipid inside the algae, said step of allowing the lipid-precipitating addition to react with the accumulated free fatty acid producing methyl ester or ethyl ester, extracting the insoluble lipid from the algae, and collecting the methyl ester or ethyl ester.

16. The method of claim 15, where the collected methyl ester or ethyl ester is collected and directly used as biodiesel without any transesterification or esterification.

17. A method for increasing the lipid content of algae comprising the steps of providing phagotrophic algae, establishing a target for a concentration of insoluble lipid to be produced within the algae, determining a ratio of glycerol and an organic acid to be combined with the algae based on the established target for the concentration of insoluble lipid to be produced within the algae, the organic acid having a chain length of from C7 to C24, after the step of establishing the target and the step of determining the ratio, simultaneously adding the glycerol and the organic acid to the algae, the organic acid being provided at a concentration of from 0.5 g/L to 10 g/L, allowing the glycerol and the organic acid to be taken in by the algae, allowing the organic acid to produce free fatty acid in the algae, allowing the glycerol to react with the free fatty acid in order to remove or reduce the self-regulation of lipid production by the algae, normally achieved by the free fatty acid, wherein the reaction between the glycerol and the organic acid forms an insoluble lipid inside the algae, and extracting the insoluble lipid from the algae.

18. A method for increasing the lipid content of algae comprising the steps of providing algae, the algae being selected from the group consisting of phagotrophic algae and osmotrophic algae, establishing a target for a concentration of insoluble lipid to be produced within the algae, determining a ratio of a lipid-precipitating addition and a salt of acetic acid to be combined with the algae based on the established target for the concentration of insoluble lipid to be produced within the algae, after the step of establishing the target and the step of determining the ratio, adding the salt of acetic acid and the lipid-precipitating addition to the algae, the lipid-precipitating addition being selected from the group consisting of glycerol, methanol, ethanol, dihydroxyethane, propanol, isopropanol, cyclopropanol, propylene glycol, butanol, isobutanol, cyclobutanol, dihydroxybutanes, trihydroxybutanal, cyclohexanol, dihydroxycyclohexanes, phenol, dihydroxybenzenes, and trihydroxybenzenes, the lipid-precipitating addition being provided at a concentration of from 1 g/L to 10 g/L, allowing the lipid-precipitating addition to be taken in by the algae, allowing the lipid-precipitating addition to react with free fatty acid inside the algae in order to remove or reduce the self-regulation of lipid production by the algae, normally achieved by the free fatty acid, wherein the reaction between the lipid-precipitating addition and the free fatty acid forms an insoluble lipid inside the algae, extracting the insoluble lipid from the algae.

* * * * *